(12) United States Patent
Walker

(10) Patent No.: US 7,499,810 B1
(45) Date of Patent: Mar. 3, 2009

(54) INDUCTIVE PROBE CONTROLLER/CONDUCTIVE PROBE EMULATOR

(75) Inventor: Stephen A. Walker, Irvine, CA (US)

(73) Assignee: Knight, LLC., Lake Forest, CA (US)

( * ) Notice: Subject to any disclaimer, the term of this patent is extended or adjusted under 35 U.S.C. 154(b) by 334 days.

(21) Appl. No.: 10/949,167

(22) Filed: Sep. 24, 2004

Related U.S. Application Data

(60) Provisional application No. 60/506,806, filed on Sep. 29, 2003.

(51) Int. Cl.
*G06F 3/01* (2006.01)

(52) U.S. Cl. ............................ 702/31; 702/22; 702/30; 702/182; 702/183

(58) Field of Classification Search ............... 702/31, 702/64, 81, 104, 134, 155, 182, 30, 33, 50, 702/183; 340/853.3; 530/358; 700/9; 705/1
See application file for complete search history.

(56) References Cited

U.S. PATENT DOCUMENTS

| | | | | |
|---|---|---|---|---|
| 4,733,798 A * | 3/1988 | Brady et al. | .................. | 222/23 |
| 4,773,798 A | 9/1988 | Gaster et al. | ................ | 408/102 |
| 4,971,714 A | 11/1990 | Lokkesmoe et al. | ......... | 510/222 |
| 4,975,137 A | 12/1990 | Cross | ......................... | 156/223 |
| 5,722,441 A * | 3/1998 | Teramoto | ................. | 134/56 R |
| 5,826,749 A * | 10/1998 | Howland et al. | ............... | 222/1 |
| 5,851,108 A * | 12/1998 | Clymer et al. | ............. | 417/44.1 |
| 5,854,557 A | 12/1998 | Tiefnig | ....................... | 324/700 |
| 6,319,420 B1 | 11/2001 | Dow | .......................... | 216/86 |
| 6,423,280 B1 | 7/2002 | Tarara et al. | ................ | 422/261 |
| 6,529,127 B2 * | 3/2003 | Townsend et al. | ........... | 340/505 |
| 6,792,637 B2 * | 9/2004 | Reichold et al. | ............... | 8/159 |
| 6,892,143 B2 * | 5/2005 | Howes et al. | ................. | 702/31 |
| 2002/0096537 A1 | 7/2002 | Gardner, Jr. | .................. | 222/52 |
| 2003/0012081 A1 | 1/2003 | Jungmann et al. | ........... | 366/141 |
| 2005/0149273 A1* | 7/2005 | Peterson et al. | ............... | 702/31 |

\* cited by examiner

*Primary Examiner*—Eliseo Ramos Feliciano
*Assistant Examiner*—Felix E Suarez
(74) *Attorney, Agent, or Firm*—Stout, Uxa, Buyan & Mullins, LLP; Donald E. Stout

(57) ABSTRACT

An Inductive Probe/Conductive Probe Emulator is designed to replace conductive probes at a much lower cost than existing inductive probe systems. The conductivity probe simulator is usable with any industrial controller that uses a standard two wire conductivity probe interface. A continuously variable semiconductor resistive element is employed to match the conductivity of any conductive probe. The system uses the inductive probe reading to adjust the resistive element to the correct value. The conductivity probe simulator can be configured to emulate any conductivity probe with any probe constant by downloading configuration parameters to the probe controller or by setting configuration switches on the controller module. Additionally, the inventive probe simulator is equipped with an embedded temperature sensing element, giving the system a capability to perform a temperature correction in the controller section, if necessary.

12 Claims, 3 Drawing Sheets

INDUCTIVE PROBE CONTROLLER/CONDUCTIVE PROBE EMULATOR

This application claims the benefit under 35 U.S.C. 119(e) of the filing date of Provisional U.S. Application Ser. No. 60/506,806 and filed on Sep. 29, 2003, which application is expressly incorporated herein by reference This invention relates generally to methods and apparatus for controlling the concentration of a chemical solution, and more particularly to methods and apparatus for controlling the concentration of a chemical solution by measuring the conductivity of the solution and taking appropriate remedial action.

BACKGROUND OF THE INVENTION

There are numerous applications in Industrial Process Control that require the measurement of the conductivity of a water-based solution. One such application is disclosed in U.S. Pat. No. 4,733,798, which is herein expressly incorporated by reference. This type of system is related to institutional ware washing and dishwashing machines, and the like. In such systems, automatic detergent dispensers are employed, for dispensing additional detergent into the wash water during a wash cycle, upon detection that the detergent level in the water has fallen below a desired value.

The conductivity of a water-based solution is often a direct analog of the concentration of dissolved chemicals in the solution. In cases where the concentration of certain chemicals in the solution is critical to successful operation, continuous real-time measurement and control is required. Conductive probes with exposed electrodes are the most common method for measuring conductivity. They are inexpensive and the interface electronics are simple, but all suffer from inherent contamination and corrosion of the exposed conductive electrodes. More caustic chemicals cause more rapid degradation. Corrosion and plating of the conductive probe electrodes cause significant measurement errors and necessitate frequent servicing to clean or replace the probe assembly.

Inductive Probe systems have been created to address the inherent problems with conductive probes but their much greater cost has seriously limited their applications, especially with traditionally low-cost chemical control systems.

What is needed, therefore, is a system for emulating conductive probe systems which is inexpensive and permits the elimination of conductive probes in new chemical control systems, and the replacement of conductive probes in existing installed systems.

SUMMARY OF THE INVENTION

The Inductive Probe/Conductive Probe Emulator of the present invention is designed to replace conductive probes at a much lower cost than existing inductive probe systems. The conductivity probe simulator of the invention is usable with any industrial controller that uses a standard two wire conductivity probe interface. A novel continuously variable semiconductor resistive element is employed to match the conductivity of any conductive probe. The system uses the inductive probe reading to adjust the resistive element to the correct value, and is equipped with the most advanced electronics and software to perform this function.

The conductivity probe simulator of the present invention can be configured to emulate any conductivity probe with any probe constant by downloading configuration parameters to the probe controller or by setting configuration switches on the controller module. Additionally, the inventive probe simulator is equipped with an embedded temperature sensing element, giving the system a capability to perform a temperature correction in the controller section and to transmit the corrected reading to the external industrial controller.

The inventive system is accurate over four orders of magnitude, from 10.0 micro-siemens to 1000.0 milli-siemens, in a preferred embodiment.

It should be noted that the chemical to be measured and controlled must be conductive, which means that in water the chemical must dissociate into ions (like NaOH will dissociate into Na+ and OH−). To measure accurately, the conductivity of the solution should be between 100 micro-siemens/cm and 1000 milli-siemens/cm. Also, the dissolved chemical must exhibit a consistent graph of concentration vs. conductivity in solution. The graph can be linear or non-linear, as long as it is consistent such that it can be described by a polynomial or a look-up table. If concentration vs. conductivity is predictable, it is possible to automatically control the concentration in a closed loop system.

Another unique feature of the present invention is a bi-directional synchronous serial data and control (bus) interface, for transmitting converted conductivity and temperature information thereover between the microprocessor (controller) of the present inventive system and an Industrial Controller host which uses the transmitted data to control chemical concentration and temperature of the monitored solution. The controller electronics are mounted in-line in the inductive sensor cable a few inches from the inductive probe. This provides for minimum noise interference between the probe and the control electronics. The overall cable length has no effect on the accuracy of the measurements.

Advantageously, the inventive system is usable to replace conductive probes in both new chemical control systems, as well as many existing systems, since the system is modular in nature, and can replace the conductive probe of the existing system as a unit. Because the sensor that is immersed in the solution does not have exposed conductive elements, and the covering is impervious to most chemicals, it does not degrade with time. The accuracy of the measured conductivity thus does not degrade with time. Thus, it will replace conductive probe sensors in many applications where the initial higher cost is far less than the lifetime cost of frequent servicing and replacement of conductive sensors.

The invention, together with additional features and advantages thereof, may be best understood by reference to the following description taken in conjunction with the accompanying illustrative drawings. In these accompanying drawings, like reference numerals designate like parts throughout the figures.

DESCRIPTION OF THE PREFERRED EMBODIMENT

Figure 1:
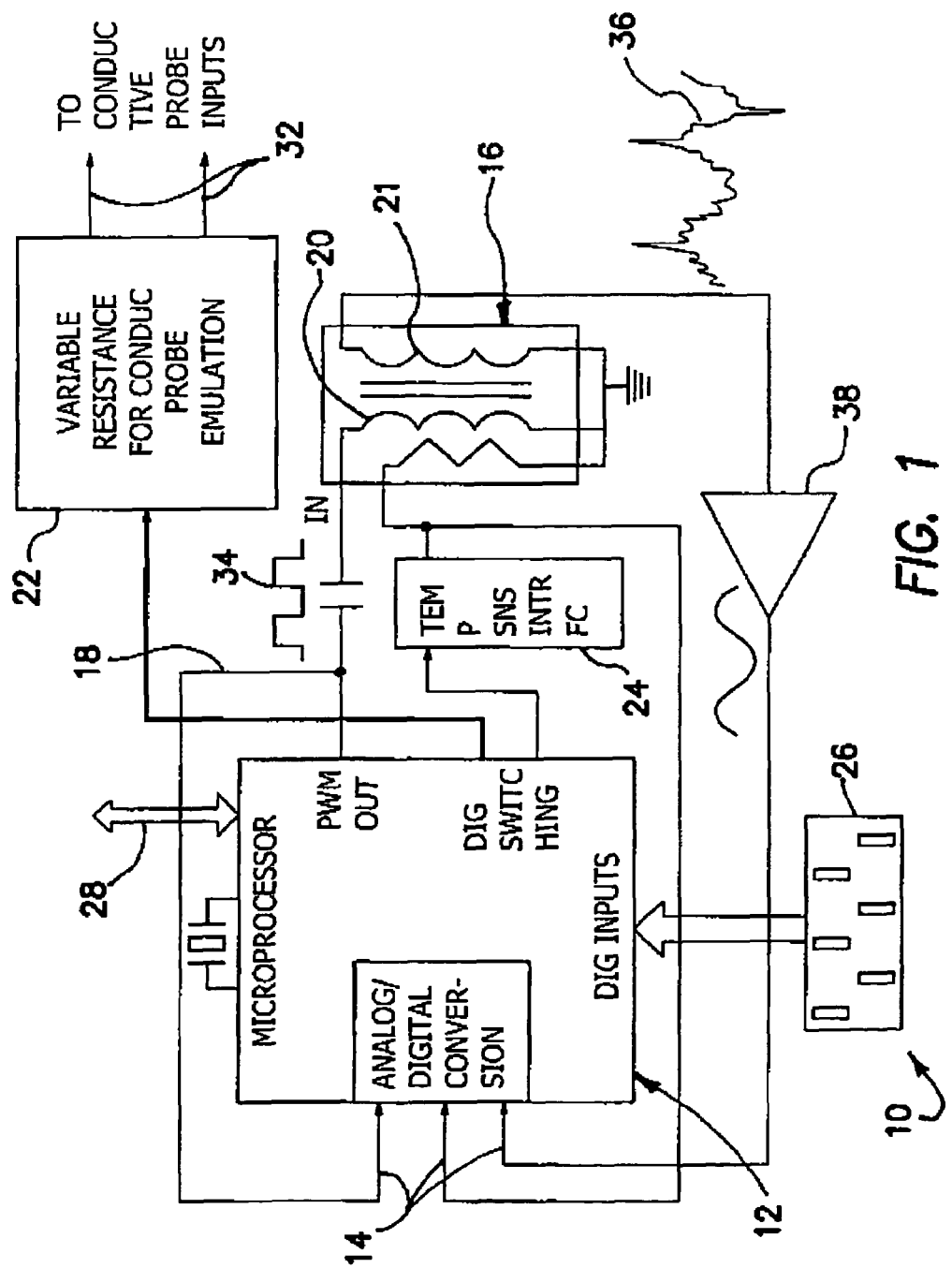
FIG. 1 is a schematic view of the inventive inductive probe system.

Referring now more particularly to FIG. 1, the inventive inductive probe controller/conductive probe emulator system 10 is illustrated. The system 10 uses a single-chip micro controller 12 as the controlling element (the toroidal controller/transmitter) of the circuit. The single-chip micro-controller 12 includes an integrated FLASH memory for storing an embedded software program for operating the system 10, EEPROM memory for storing calibration constants and other data, and multiple Analog to Digital input ports 14 for converting analog signals from a toroidal probe 16. The toroidal probe 16 preferably includes an optional temperature sensor, the signals from which are also converted by the ports 14, from analog to digital values.

The toroidal probe 16, and related sensor, are available in the market, from, for example, Sensorex of Garden Grove, Calif., Honeywell, Cole-Parmer, Rosemount Analytical, Foxboro, or Walchem, for example. Specifications for suitable probe products presently favored by the inventor are attached hereto in an appendix.

Additional features of the inventive system 10 include a pulse-width modulated output port 18 for driving a primary coil (or wire-wound toroid) 20 of the inductive probe 16, which also comprises a secondary coil 21. The two wire-wound toroids or coils are isolated from the solution to be measured. One toroid acts as the transmitter and the other as the receiver. The inductive sensor is immersed in the liquid and the sensor interface circuit provides sensor excitation and feedback measurement. The controller/transmitter energizes the transmitter toroid, inducing an electric current into the solution that induces an electric current into the receiver toroid. The strength of that induced current is directly proportional to the conductivity of the solution.

Multiple digital input and output ports are provided for controlling a variable conductive resistance 22, controlling a temperature sensor interface 24, and reading inputs from a configuration switch 26.

Figure 2:
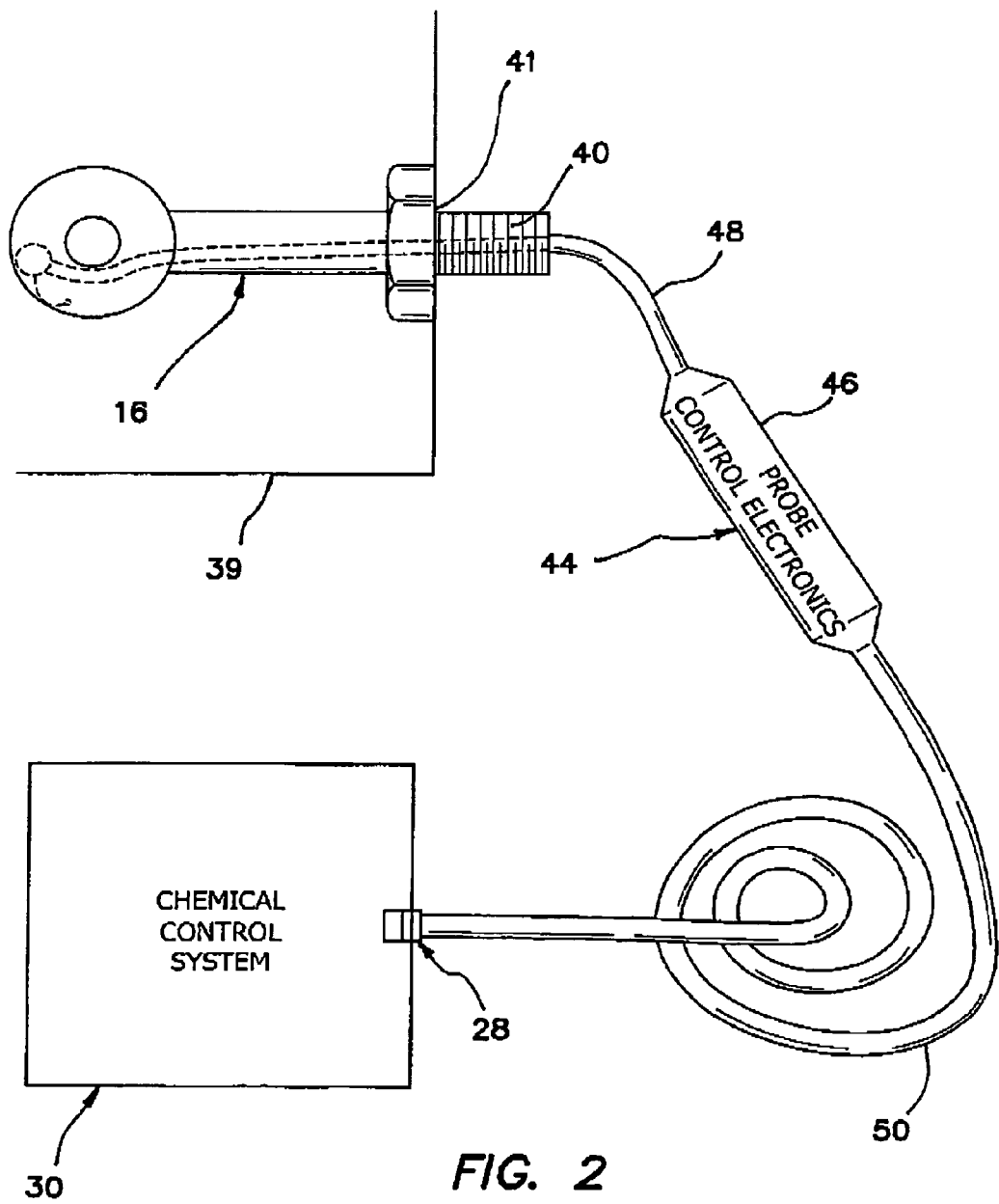
FIG. 2 is a schematic view of one application for the inventive inductive probe system of FIG. 1.
Figure 3:
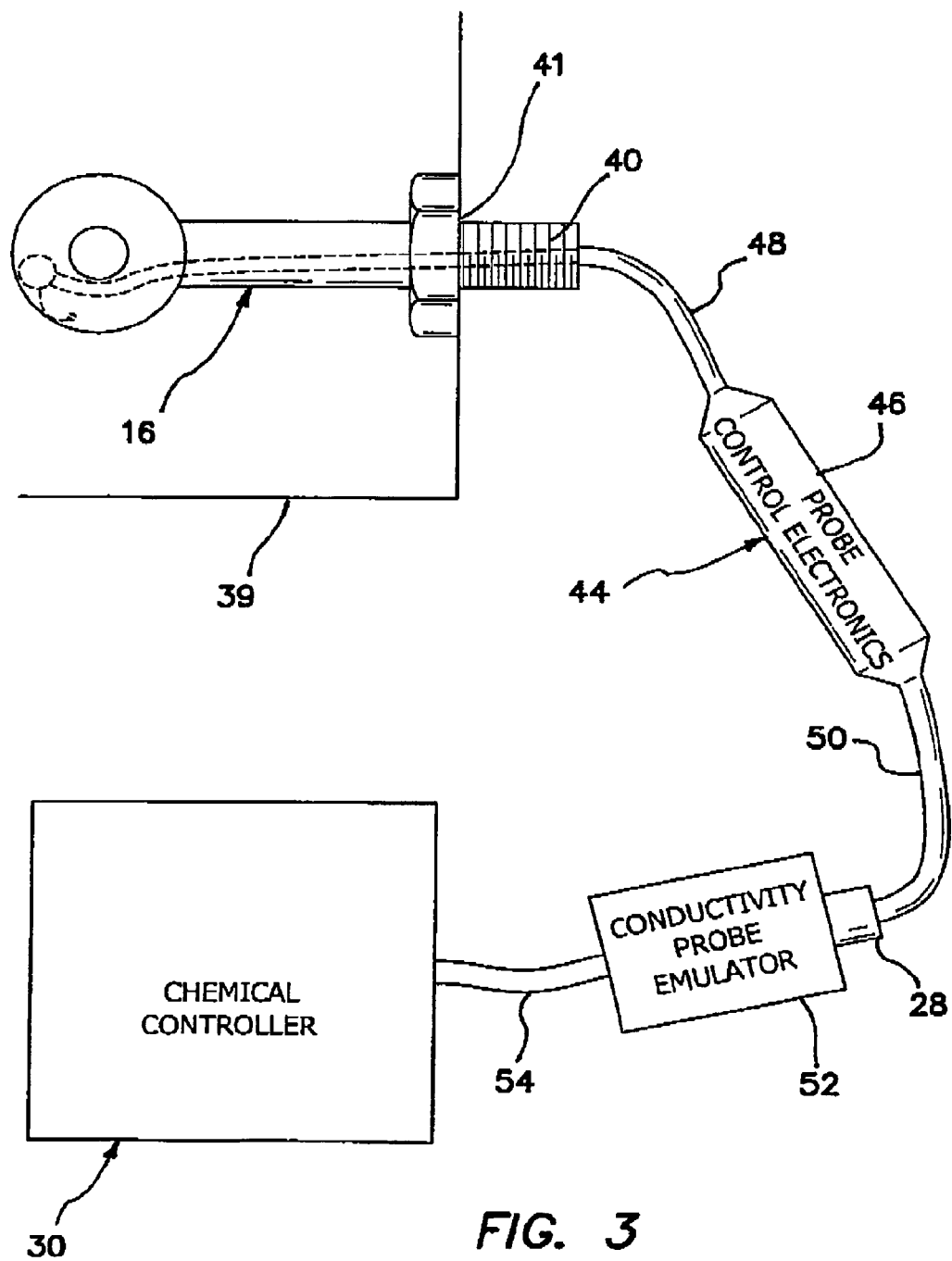
FIG. 3 is a schematic view, similar to FIG. 2, of a second application for the inventive inductive probe system of FIG. 1.

A standard bi-directional serial interface bus 28 is provided for communicating with, and transmitting conductivity and temperature data to, a remote computer or dedicated controller 30 (see FIGS. 2 and 3).

The modified serial interface bus 28, advantageously, is infinitely expandable, and builds into the inventive system 10 a modular "plug and play" capability. The system employs distributed intelligence, comprising local ID chips in each unit, rather than all of the intelligence in a central processor.

The inventive device can be pre-calibrated at the factory to work with multiple inductive probe devices that have different probe constants (i.e. the output signal vs. input signal for the same concentration level differs for each device). This will be discussed in greater detail below, in connection with discussion regarding the embodiments of FIGS. 2 and 3. It can also be pre-calibrated at the factory to output different resistance values for the same conductivity reading in order to make it compatible with different chemical controllers from multiple vendors.

After the connections shown in FIG. 1 are made and power is applied to the circuit, the micro controller 12 will automatically read the configuration dip switches 26 to determine the nature and characteristics of the inductive probe 16 which has been connected to the circuit. The switches 26 also indicate which chemical controller 30 is connected to the variable resistance outputs (conductive probe inputs) 32. This information is used by the micro controller 12 to select the correct probe constant and variable resistance graph or look-up table stored in its EEPROM memory. Importantly, once the configuration switches 26 are set to the correct positions, the device automatically configures itself, using the embedded software program in its FLASH memory, with no adjustments required by the end-user.

After power is applied, the device will also begin generating a fixed frequency square wave 34 to the primary (or input) coil 20 of the inductive probe 16. If the inductive probe is immersed in a liquid solution that contains a chemical that has dissolved into positive and negative ions, the amplitude of the toroid probe output signal 36 will be directly proportional to the concentration of positive and negative ions.

Since the output signal level will be much lower than the input for low chemical concentration levels and will be susceptible to noise pickup, voltage spikes, and harmonic distortion, it is necessary to filter and amplify the signal. An active band pass filter and amplifier 38 is provided for the purpose of removing most of the noise and harmonics, but it is not fast enough to remove the high amplitude voltage spikes.

In order to remove the large voltage spikes, and to further amplify and accurately measure the toroid output signal 36, the improved signal at the filter and amplifier 38 is input to one of the micro controller sample & hold inputs 14, where it is sampled and converted to the equivalent digital value at greater than the required Nyquist sampling rate. The samples are stored in the microprocessor RAM where proprietary software removes the spikes and runs a Chebyshev Band pass filter algorithm to take out the DC level and remaining harmonics. The software then computes the Root Mean Square (RMS) value of the samples and stores this value as the input signal. The RMS computation is a more accurate determination of the total energy in the signal.

The input square wave 34 is also connected to a Digital to Analog converter input 14 of the microcomputer 12, and is sampled and digitized at much greater than the Nyquist rate. This yields the fundamental frequency and amplitude. The filtered values are stored in the microcomputer RAM. The RMS value of these values is computed and stored in RAM.

Software then computes the RMS output to RMS input ratio and this value is used in a linear equation to determine the actual conductivity of the sampled liquid.

The microcomputer 12 also turns on the temperature sensing component in the probe 16, by turning on the temperature sensor interface circuitry 24. The output of the temperature sensor is also connected to one of the Analog to Digital inputs 14, where it is digitized and used to compute the actual temperature based on an empirically determined equation stored in the EEPROM memory. The measured temperature is used to adjust the conductivity reading relative to 25 degrees C., to give a temperature compensated reading.

The microcomputer 12 will transmit the latest conductivity reading (in milli-siemens) to the host device that is connected to the standard serial interface 28 whenever the host computer (or controller) 30 requests a reading. Importantly, the device is designed to continuously adjust the variable resistance 22 to reflect the actual measured conductivity of the solution. It can modify the variable resistance to have an offset and/or scaling factor relative to the actual conductivity of the solution if this is required to yield an accurate reading on the chemical controller 30 that is reading the output of the variable resistance 22 at the outputs 32. Since the configuration switch inputs 26 indicate the nature of the chemical device that is connected to the variable resistance outputs 32, the software can use an equation or lookup tables stored in program code to determine any required correction to the actual conductivity reading.

An advantageous feature of the present inventive system 10 is that it eliminates the need for two hardware RMS to DC converters, a precision hardware sine wave generator, multiple potentiometers for gain and frequency adjustments, a hardware analog divider, span adjust, and hardware temperature compensation. Furthermore, the inventive microcomputer 12 can adjust the output square wave frequency under software control to provide optimum response of the inductive probe and external bandpass filter.

As noted above, to summarize, the controller/transmitter communicates with the main controller 30, and transmits calibrated conductivity data to the main controller over the Standard Interface Bus 28. The inductive sensor is normally used as the feedback element in a closed loop chemical control system. It can be used in warewash, laundry, and may industrial applications.

The non-contacting toroidal sensor technology of the present invention eliminates contamination and calibration issues that are inherent in direct contacting conductivity sensors. The conductivity measurement is extremely reliable, the sensor is immune to thin coatings and probe corrosion that always causes degradation with direct contacting sensors. Inductive sensors can measure a much wider range of conductivity. Outer sensor materials such as PEEK™ result in excellent mechanical strength, high temperature capability, and resistance to chemical attack.

In operation, to summarize, when DC power is applied to the toroidal controller/transmitter 10, it automatically reads the input and output of the toroidal probe 16, if the probe is connected, and continuously computes the conductivity of the solution based on the ratio of probe output to input signal level using an empirically determined transfer function Y (conductivity)=f(x), wherein x is the ratio of output to input toroidal signal amplitude. The controller/transmitter automatically sets the gain of the feedback loop to maintain an adequate signal-to-noise ratio and to keep amplified output signal in the linear active region. It reads the configuration switches 26 to ensure that they are set to the correct positions, and the device 10 automatically configures itself with no adjustments required by the end-user.

The microcomputer 12 transmits the latest reading (in milli-siemens) to the host device that is connected to the standard serial interface 28 whenever the host computer/controller 30 requests a reading.

If a temperature probe is connected, the controller/transmitter automatically reads the temperature and provides temperature compensation of the conductivity reading based on a 25 degree C. baseline. The device continuously adjusts the variable resistance 22 to reflect the actual measured conductivity of the solution. It can modify the variable resistance 22 to have an offset and/or scaling factor relative to the actual conductivity of the solution if this is required to yield an accurate reading on the chemical controller 30 that is reading the output of the variable resistance 22. Since the configuration switch inputs 26 indicate what chemical device is connected to the variable resistance outputs 32, the software can use an equation or lookup tables stored in program code to determine any required correction to the actual conductivity reading.

The inventive system is applicable to a number of systems, including, for example, ware washing machines such as those disclosed in U.S. Pat. No. 4,733,798, herein expressly incorporated by reference, as noted above. The inventive system comprises a proportional integral differential (PID) system, meaning that the system continuously evaluates the concentration of desired chemicals in the solution being treated, relative to a desired concentration, and additionally evaluates the rate of change of concentration and the error dwell time. All of this information is utilized by the PID system in deriving its determination as to when the solution concentration is increased, and at what rate. A pulsing modality is utilized to increase the solution concentration, rather than a steady-state replenishment (chemical injection) rate. This pulsing modality takes place during the entire operational cycle.

Referring now to FIG. 2, there is shown one potential embodiment which uses the inventive system 10, wherein the toroidal probe 16 is disposed within a tank 39 full of solution (not shown) to be measured and controlled. A tank mounting stud 40 is adapted to extend through a mounting hole 41 in the tank, and to be mounted therethrough using a fastener 42, so that the probe 16 is secured within the tank. The probe control electronics 44 comprises most of the system 10 shown in FIG. 1, including the microprocessor/controller 12, temperature sensor interface 24, variable conductive resistance 22, dip switches 26, and other components. This unit 44 is contained in a generally cylindrical shaped housing 46, which is sized so that it fits through the mounting hole 41, so that the probe 16 can be easily positioned within the tank 39. In a preferred embodiment, a 4 inch cable 48 connects the electronics 44 to the probe 16. The opposing end of the housing 46 is connected to the remote computer or dedicated controller 30, through the smart IC serial communications interface 28, via a cable 50, which in the illustrated embodiment is about 25 feet in length.

Referring to FIG. 3, an embodiment alternative to that of FIG. 2 is illustrated, which is different from FIG. 2 in that a conductivity probe emulator 52 is employed. The probe electronics 44 are connected to the conductivity probe emulator 52 via cable 50 and the smart IC serial communications interface 28, with the conductivity probe emulator 52, in turn, being connected to the controller 30 via a two wire conductivity probe input 54.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An inductive probe controller/inductive probe emulator system, comprising:
    an inductive probe for disposition in a solution;
    a micro-controller having multiple analog to digital input ports and having a plurality of output ports said micro-controller being connected to said inductive probe; and
    a variable conductive resistance connected to said micro-controller for receiving control inputs from the micro-controller and having conductive probe outputs;
    wherein said system is capable of being configured to emulate any of a number of different conductivity probes with any of a number of different probe constants by downloading configuration parameters to the probe controller or by setting configuration switches in said system.

2. The system as recited in claim 1, and further comprising a chemical controller connected to said micro-controller.

3. The system as recited in claim 2, wherein said micro-controller is disposed within a housing separate from said inductive probe.

4. The system as recited in claim 3, wherein said housing is generally cylindrical.

5. The system as recited in claim 3, and further comprising a cable connecting said inductive probe to said housing.

6. The system as recited in claim 5, wherein both said inductive probe and said housing are sized and configured to be insertable through a mounting hole in a tank containing said solution.

7. The system as recited in claim 6, and further comprising a second cable for connecting said housing to said chemical controller.

8. The system as recited in claim 2, and further comprising a conductivity probe emulator.

9. The system as recited in claim 8, wherein said conductivity probe emulator is connected between said chemical controller and said probe micro-controller.

10. The system as recited in claim 1, and further comprising a temperature sensor.

11. The system as recited in claim 1, wherein said inductive probe comprises a primary coil and a secondary coil.

12. The system as recited in claim 2, and further comprising a bi-directional serial interface bus connecting said micro-controller to said chemical controller.

* * * * *